United States Patent
Twomey

(10) Patent No.: US 9,526,563 B2
(45) Date of Patent: Dec. 27, 2016

(54) SPINDLE ASSEMBLY WITH MECHANICAL FUSE FOR SURGICAL INSTRUMENTS

(75) Inventor: John R. Twomey, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 1176 days.

(21) Appl. No.: 13/441,169

(22) Filed: Apr. 6, 2012

(65) Prior Publication Data

US 2013/0267951 A1 Oct. 10, 2013

(51) Int. Cl.
*A61B 18/18* (2006.01)
*A61B 18/14* (2006.01)
*A61B 17/29* (2006.01)
*A61B 1/00* (2006.01)

(52) U.S. Cl.
CPC .......... *A61B 18/1445* (2013.01); *A61B 1/0008* (2013.01); *A61B 18/1447* (2013.01); *A61B 2017/294* (2013.01); *A61B 2017/2936* (2013.01); *A61B 2017/2946* (2013.01); *A61B 2018/1455* (2013.01); *A61B 2090/034* (2016.02)

(58) Field of Classification Search
CPC ............... A61B 2018/1455; A61B 2017/2936; A61B 2017/294; A61B 2017/2946; A61B 18/1447; A61B 1/0008
See application file for complete search history.

(56) References Cited

U.S. PATENT DOCUMENTS

| | | | |
|---|---|---|---|
| 6,494,881 B1 * | 12/2002 | Bales | A61B 18/149 606/41 |
| 7,001,382 B2 | 2/2006 | Gallo, Sr. | |
| 2007/0043353 A1 * | 2/2007 | Dycus et al. | 606/51 |
| 2008/0029577 A1 * | 2/2008 | Shelton et al. | 227/176.1 |
| 2009/0138006 A1 | 5/2009 | Bales et al. | |
| 2009/0240246 A1 | 9/2009 | Deville et al. | |
| 2010/0286791 A1 | 11/2010 | Goldsmith | |

* cited by examiner

*Primary Examiner* — William Levicky
*Assistant Examiner* — Lindsey G Hankins

(57) ABSTRACT

A spindle assembly of a surgical instrument is provided which includes a body and a cutter pin. The body has at least one wall forming first and second channels therein. The cutter pin is disposed within the second channel and operably coupled to a knife rod extending therethrough and is operatively coupled at its distal end to a knife. When the knife rod is moved between a retracted position and a deployed position, the spindle assembly is moved between a first and a second position along the shaft. The cutter pin is configured to deform and exit the body when the knife is deployed and disposed in a trapped condition and in response to an applied force, thereby decoupling the knife from the spindle assembly.

8 Claims, 9 Drawing Sheets

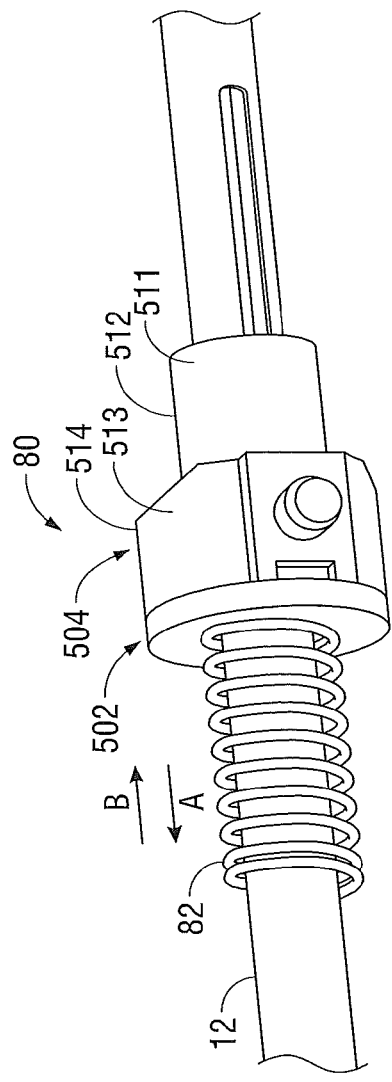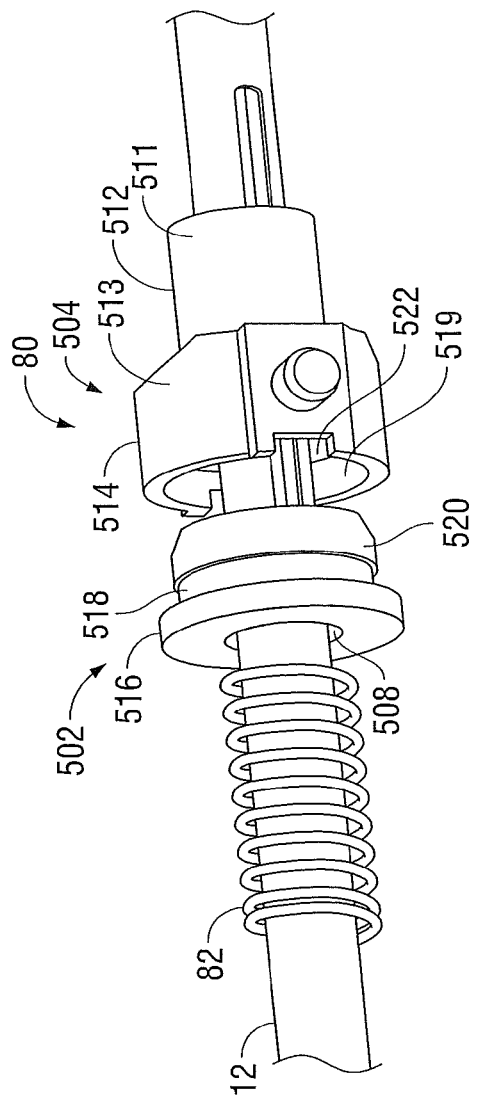

SPINDLE ASSEMBLY WITH MECHANICAL FUSE FOR SURGICAL INSTRUMENTS

BACKGROUND

The present disclosure relates to surgical instruments. More particularly, the present disclosure relates to a spindle assembly having a mechanical fuse that causes a surgical instrument to failsafe under certain surgical conditions.

TECHNICAL FIELD

Electrosurgical instruments, e.g., forceps, utilize both mechanical clamping action and electrical energy to effect hemostasis by heating tissue and blood vessels to coagulate, cauterize and/or seal tissue. As an alternative to open forceps for use with open surgical procedures that require relatively large incisions, many modern surgeons use endoscopic or laparoscopic instruments for remotely accessing organs through smaller, puncture-like incisions or natural orifices. As a direct result thereof, patients tend to benefit from less scarring and reduced healing time.

Many endoscopic surgical procedures require cutting or ligating blood vessels or vascular tissue. Due to the inherent spatial considerations of the surgical cavity, surgeons often have difficulty performing traditional methods of controlling bleeding, e.g., suturing, clamping and/or tying-off transected blood vessels. By utilizing an endoscopic electrosurgical forceps, a surgeon can cauterize, coagulate/desiccate, staple, and/or reduce or slow bleeding by applying electrosurgical energy to tissue through a pair of opposing jaw members and controlling the intensity, frequency and duration of the electrosurgical energy applied. The surgeon can seal larger vessels or tissue by clamping the vessels or tissue with the jaw members and applying electrosurgical energy to the clamped tissue. Typically, after a vessel or tissue is sealed, the surgeon advances a knife to sever the sealed tissue disposed between the opposing jaw members.

The forceps is typically provided with several actuators. A first actuator, such as a lever, controls opening and closing of the jaw members relative to one another for clamping and releasing tissue. A second actuator, such as a footswitch, controls application of the electrosurgical energy via the jaw members. A third actuator, such as a trigger, controls deployment of the knife. The forceps may be configured with a lockout feature that prevents deployment of the knife unless the jaw members are closed. Additionally, when the knife is deployed, the lockout feature may prevent the jaw members from opening.

SUMMARY

One aspect of the present disclosure relates to a surgical instrument having a housing and a shaft having a proximal end positioned within the housing and a distal end positioned remote from the housing. The shaft has a longitudinal axis defined between the proximal and distal ends. A pair of jaw members is operably coupled to the distal end of the shaft. A movable knife rod is at least partially disposed within the shaft. A knife is operably coupled to a distal end of the knife rod. An actuator is operably coupled to the jaw members and moveable relative to the housing between a first position and a second position for moving the jaw members between an open position and a substantially closed position.

A movable spindle assembly is provided which has a body which has at least one wall defining first and second channels therein. The first channel has a longitudinal orientation through which the shaft and knife rod extend. The second channel has a different orientation than the first channel and is in communication with the first channel. A cutter pin is disposed within the second channel and operably coupled to the knife rod.

A trigger is operably coupled to the spindle assembly and moveable relative to the housing between a first position and a second position for moving the spindle assembly and the knife between a retracted position in which the knife is retracted within the shaft and a deployed position in which at least a portion of the knife extends beyond a distal end of the shaft between the jaw members. When the knife is deployed and disposed in a trapped condition, the cutter pin is configured to deform and exit the spindle assembly body in response to an applied force, thereby allowing the knife to move independent of the spindle assembly.

The cutter pin may exit the second channel and further exit the spindle assembly via the first channel. The wall(s) may include a wall that defines the second channel, wherein the wall may be provided with a chamfer that facilitates the exit of the cutter pin from the second channel. One of the wall(s) may be deformable for facilitating exit of the cutter pin from the spindle assembly. The spindle assembly may include a spindle sleeve and a spindle cap that define a gap therebetween when assembled that forms the second channel.

Deformation of the cutter pin may include folding of the cutter pin about the knife rod to secure the cutter pin to the knife rod. The surgical instrument may further include a rotation assembly configured to rotate the shaft with the knife rod and the cutter pin, wherein the second channel may have an annular shape that accommodates rotation of the cutter pin. A radius of the second channel may be normal to the longitudinal axis of the shaft. Operation of one of the trigger or the actuator may cause application of the force to the spindle assembly to move the spindle assembly away from the cutter pin when the knife is in a trapped condition.

According to another aspect of the disclosure, a spindle assembly of a surgical instrument is provided. The spindle assembly includes a body and a cutter pin. The body has at least one wall forming first and second channels therein. The first channel has a first orientation and receives a shaft extending therethrough. The second channel has a second orientation different than the first orientation and is in communication with the first channel. The cutter pin is disposed within the second channel and is operably coupled to a knife rod that extends through the shaft and is further operatively coupled at its distal end to a knife.

When the knife rod is moved between a retracted position in which the knife is retracted within the shaft and a deployed position in which the knife is deployed and extends at least partially beyond a distal end of the shaft, the spindle assembly is moved between a first position and a second position along the shaft. The cutter pin is configured to deform and exit the body when the knife is deployed and disposed in a trapped condition and in response to an applied force, thereby decoupling the knife from the spindle assembly.

The cutter pin may exit the second channel and exits the body via the first channel. At least one of the walls that defines the second channel may be provided with a chamfer that facilitates the exit of the cutter pin from the second channel. At least one of the wall(s) may be deformable for facilitating exit of the cutter pin from the spindle assembly. The spindle assembly may include a spindle sleeve and a spindle cap that form a gap therebetween when assembled that forms the second channel.

Deformation of the cutter pin may include folding of the cutter pin about the knife rod to secure the cutter pin to the knife rod. The second channel may have an annular shape that accommodates rotation of the cutter pin. A radius of the second channel may be normal to the longitudinal axis of the shaft. The force may be applied to the spindle assembly in response to operation of an actuator of the surgical instrument.

BRIEF DESCRIPTION OF THE DRAWINGS

Various embodiments of the present disclosure are described herein with reference to the drawings, wherein:

FIG. 5 is an enlarged perspective view of the spindle assembly of FIGS. 2-4;

FIG. 6 is a partially exploded perspective view of the spindle assembly of FIG. 5;

DETAILED DESCRIPTION

Figure 1A:
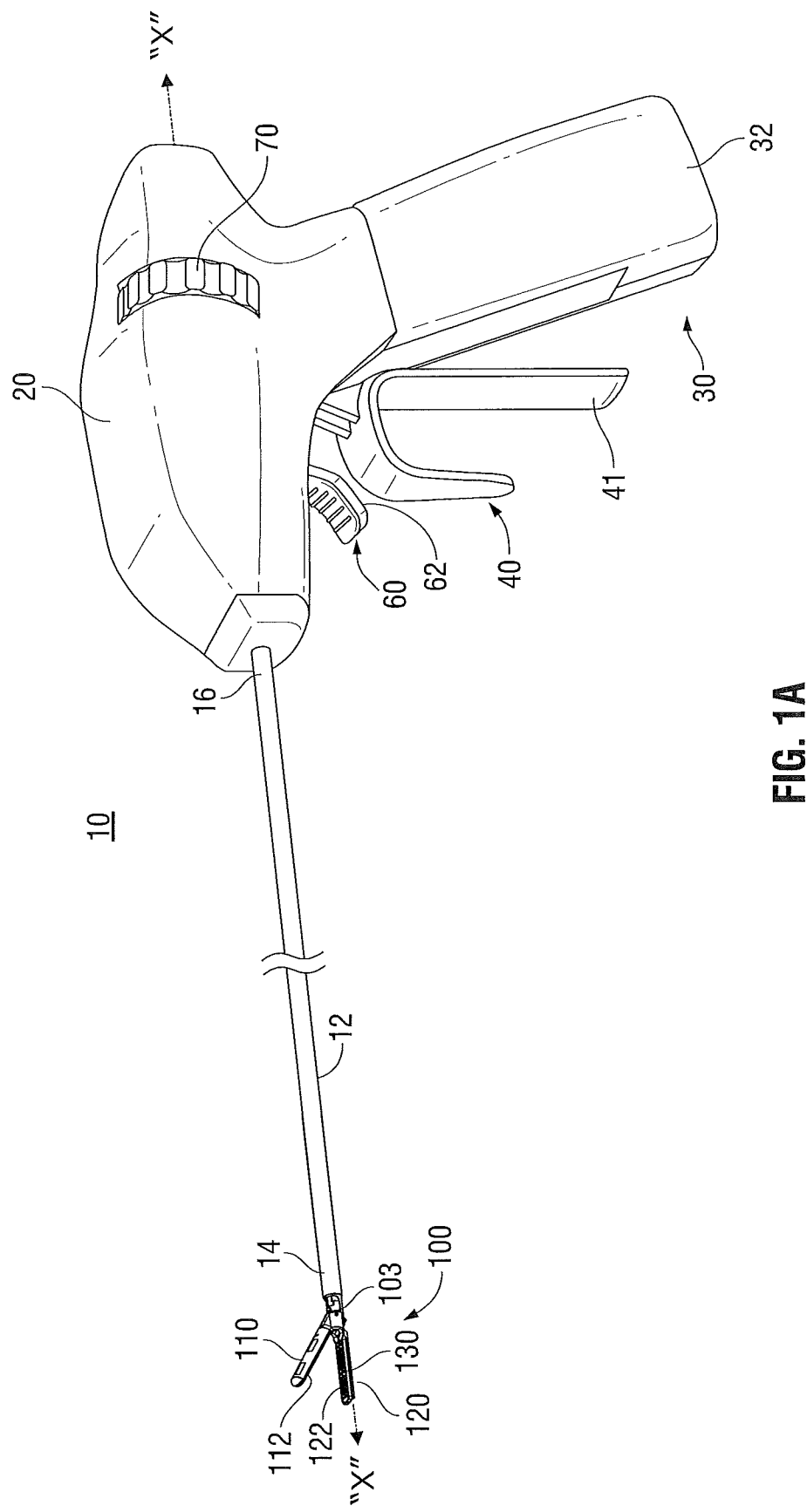
FIG. 1A is a perspective view of a forceps including an end effector assembly in accordance with an embodiment of the present disclosure wherein jaw members of the end effector assembly are disposed in an opened position.

The present disclosure provides a mechanical fuse for a surgical forceps which may be used during device lockup in which jaws of the surgical forceps have closed with a knife in a deployed position such that the knife cannot be retracted. When device lockup occurs, a surgeon may activate the mechanical fuse by applying a force to a lever that operates the jaws, or to a trigger that operates the knife, causing the forceps to fail safe. Once the forceps fails safe the knife may be moved to a retracted position for safe removal of the forceps from the surgical site.

Embodiments of the present disclosure are described in detail with reference to the drawing figures wherein like reference numerals identify similar or identical elements. As used herein, the term "distal" refers to a portion of an apparatus that is further from a user, while the term "proximal" refers to a portion of the apparatus that is closer to a user.

Figure 1B:
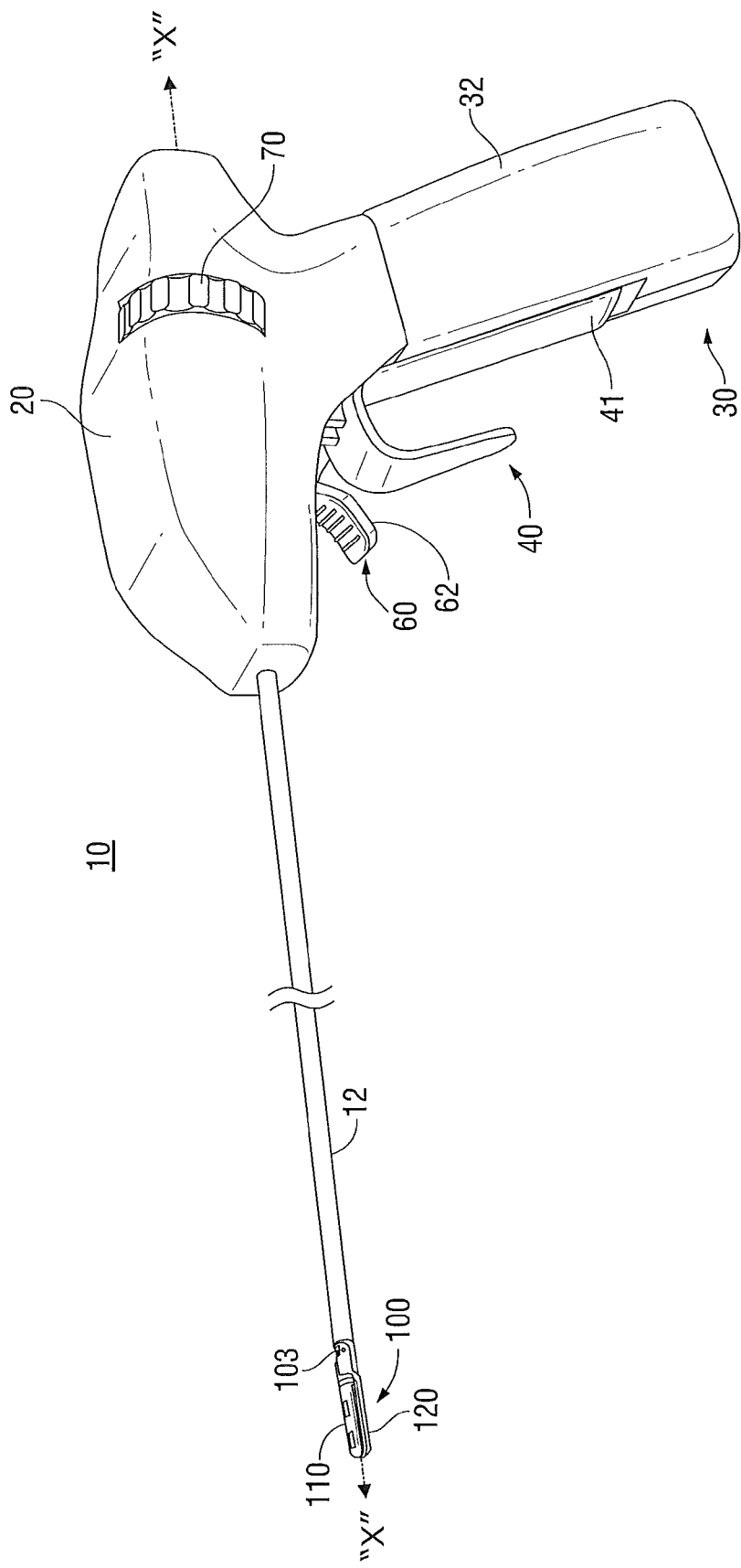
FIG. 1B is a perspective view of the forceps shown in FIG. 1A wherein the jaw members are disposed in a closed position.
Figure 1C:
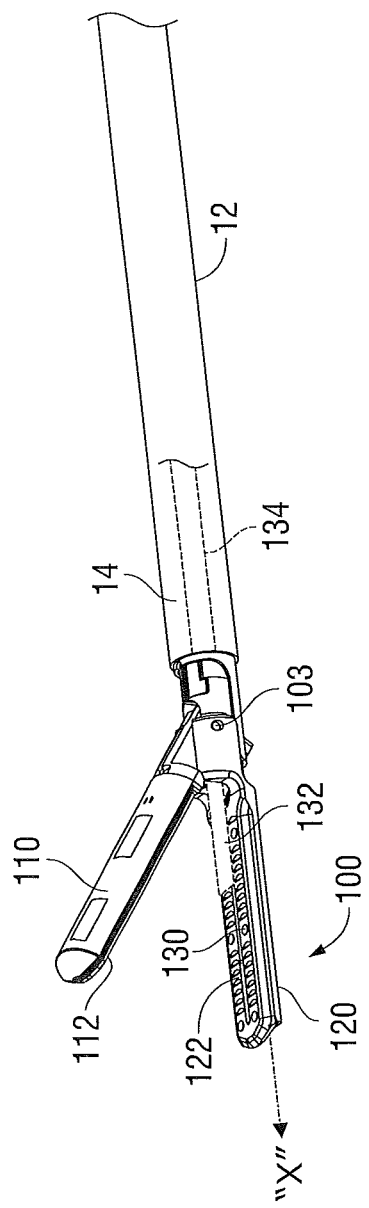
FIG. 1C is an enlarged perspective view of the end effector assembly of the forceps shown in FIG. 1A with a knife shown in broken line.

Turning now to FIGS. 1A-1C, forceps 10 is an example of an instrument for use in accordance with the present disclosure. Forceps 10 includes a housing 20, a handle assembly 30, a lever assembly 40, a trigger assembly 60, a rotating assembly 70, and an end effector assembly 100. Forceps 10 further includes a shaft 12 having a distal end 14 that mechanically engages end effector assembly 100 and a proximal end 16 that mechanically engages housing 20. The shaft 12 defines a longitudinal axis X-X extending therethrough. Alternatively, any surgical instrument having an actuator operable to control one or more functions of an end effector assembly may be provided.

End effector assembly 100 includes a pair of opposing jaw members 110 and 120. End effector assembly 100 is designed as a unilateral assembly, i.e., jaw member 120 is fixed relative to the shaft 12 and jaw member 110 is moveable about a pivot 103 relative to jaw member 120. However, either, or both jaw members 110, 120 may be moveable with respect to the shaft 12. In any of these embodiments, jaw members 110, 120 are moveable from an open position in which jaw members 110, 120 are spaced apart from one another, as shown in FIG. 1A, to a substantially closed position in which the jaw members 110, 120 are not spaced from one another or are closer to one another than in the open position, as shown in FIG. 1B. In the closed position, jaw members 110, 120 are sufficiently close to one another for grasping and manipulating tissue. Further, jaw members 110, 120 include a respective electrically conductive tissue sealing surface 112, 122. Sealing surfaces 112, 122 are disposed in opposed relation relative to one another such that, with jaw members 110, 120 in the closed position grasping tissue therebetween, electrosurgical energy may be supplied to one or both of sealing surfaces 112, 122 of jaw members 110, 120, respectively, to seal or otherwise treat tissue grasped therebetween.

Jaw members 110, 120 define a longitudinally extending knife channel 130 therein, which permits reciprocation of a knife 132 therethrough for dividing tissue grasped between the jaw members 110, 120. Knife 132 is operatively coupled to a knife rod 134 that is received within a longitudinally oriented channel defined within shaft 12. Knife rod 134 is operatively coupled to trigger assembly 60 such that, upon actuation of a trigger 62, the knife 132 is translated from a retracted position to an extended position wherein at least a portion of the knife 132 is advanced beyond a distal end of shaft 12 between jaw members 110, 120 to cut tissue grasped therebetween. As described below with reference to FIGS. 3-4, trigger 62 is biased toward an initial position (see FIGS. 2-3) by a spring 82, such that upon release of trigger 62, the knife 132 is returned to its initial, retracted position. Forceps 10 may be designed to withstand about 200-500 knife snap-back cycles.

As described further below, a lockout feature prevents the knife 132 from being deployed when the jaw members 110, 120 are in the open position. With reference to FIG. 1C, knife 132 is shown in broken lines to indicate that the lockout feature would prevent knife 132 from actually being deployed to the position shown when the jaw members 110, 120 are in the open position. Additionally, the jaw members 110, 120 are prevented from being opened via the normal course of operation while the knife 132 is deployed.

As described further below, in some circumstances, a device "lockup" condition can occur in which the knife 132 is deployed but trapped or immobilized between the jaw members 110, 120 when in the closed position. With the knife "locked up", the jaw members 110, 120 may not be able to be opened via the normal course of operation. It may be difficult to remove the forceps 10 from a surgical site when a device lockup condition occurs, particularly when the jaw members 110, 120 are clamped about tissue.

Figure 7:
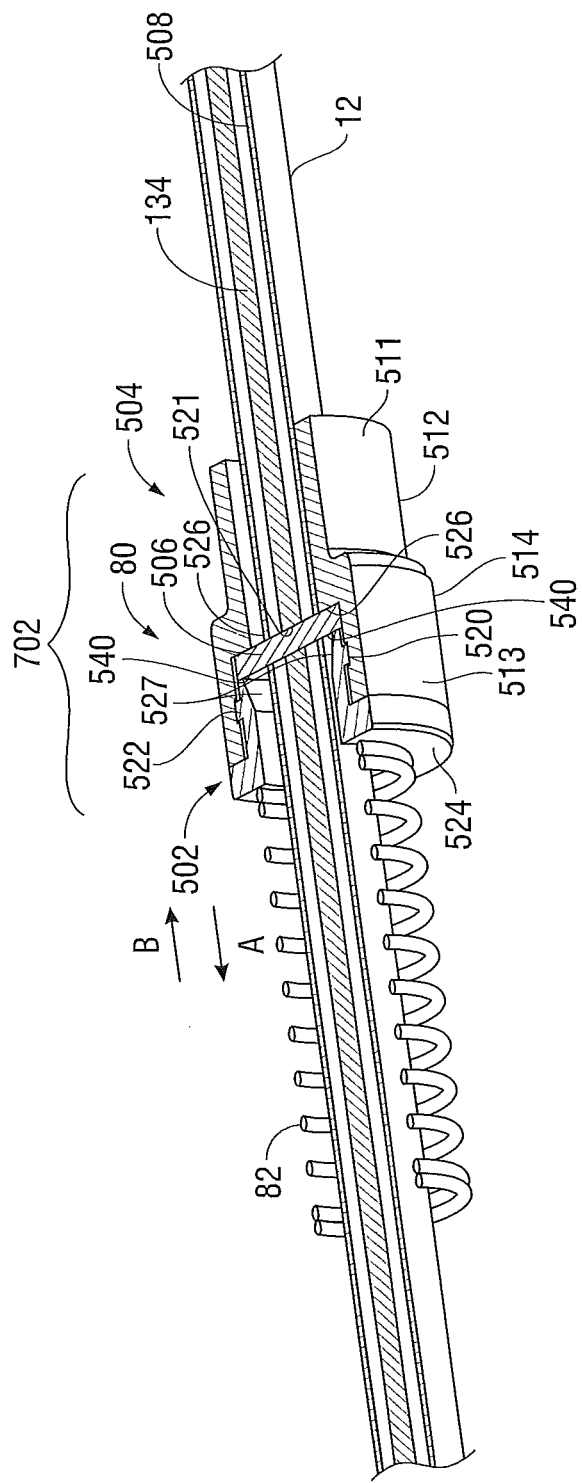
FIG. 7 is a cross-sectional perspective view of the spindle assembly of FIG. 5.
Figure 8:
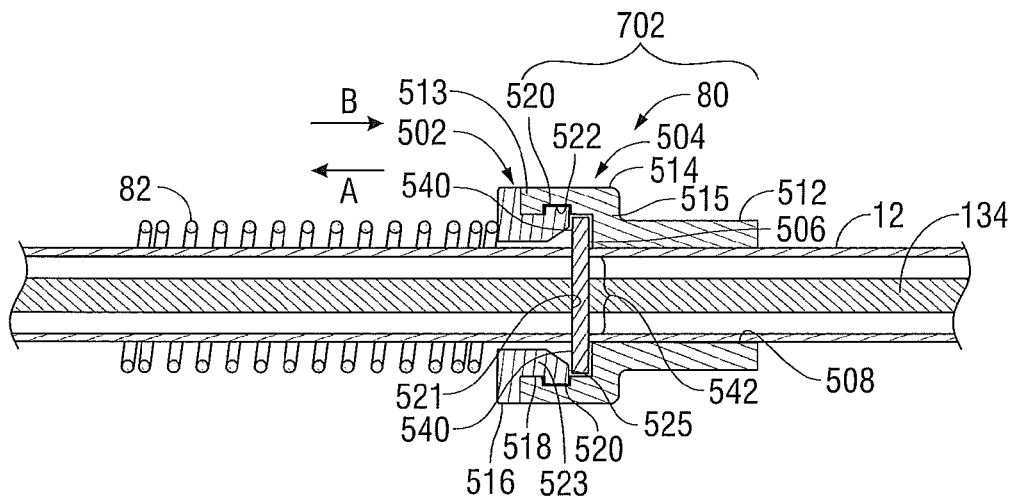
FIG. 8 is a cross-sectional side view of the spindle assembly of FIG. 5 with a cutter pin in an initial position, wherein a failsafe condition has not occurred.
Figure 9:
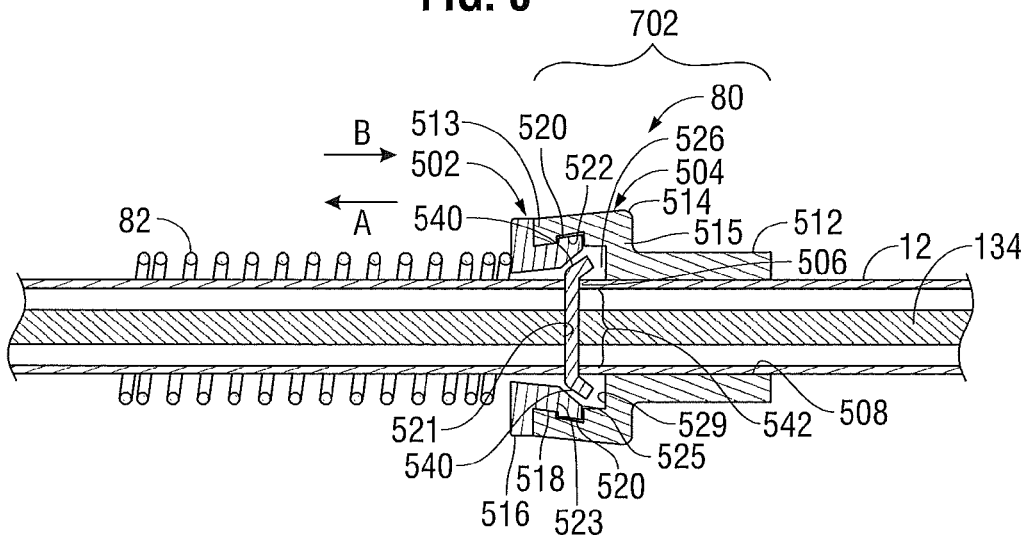
FIG. 9 is a cross-sectional side view of the spindle assembly of FIG. 5 with the cutter pin in an intermediate position, exiting the spindle assembly, when the failsafe condition has occurred.

The present disclosure provides a mechanical fuse 702 (see FIG. 7), described in detail below, for use during device lockup. The mechanical fuse 702 allows the forceps 10 to failsafe in a predictable manner and allows the surgeon to open the jaw members 110, 120 and safely disengage the forceps 10 from the surgical site.

In some embodiments (not shown), one or both of the jaw members 110, 120 and/or the knife 132 may be configured to curve to the left or the right to improve visibility of the jaw members 110, 120 and the tissue during interaction with tissue. The knife 132 is guided along knife channel 130 to curve in the intended direction.

Rotating assembly 70 is integrally associated with housing 20 and is rotatable in either direction about longitudinal axis X-X to rotate jaw members 110, 120 with respect to housing 20 about longitudinal axis X-X. Other configurations of rotating assembly 70 are envisioned (e.g., the rotating assembly 70 positioned externally from the housing 20). Rotation of rotating assembly 70 causes rotation of shaft 12. Knife rod 134 rotates together with shaft 12.

Handle assembly 30 includes an integral handle 32 which extends from housing 20, and, in some embodiments (not shown), may be configured to releasably engage housing 20. Handle assembly 30 is ergonomically configured such that a surgeon may grasp handle assembly 30 and operate lever assembly 40, trigger assembly 60, and/or rotating assembly 70 with a single hand. Handle assembly 30 may further include a battery pack (not shown) disposed within a battery housing defined in integral handle 32 that provides power to forceps 10. The battery pack may be configured to electrically couple to a generator (not shown) disposed within housing 20 for supplying electrosurgical energy to the sealing surfaces 112, 122 of jaw members 110 and 120. Alternatively, forceps 10 may be configured to be coupled to an external power source (not shown) and/or generator (not shown), e.g., via an electrosurgical cable (not shown).

Figure 2:
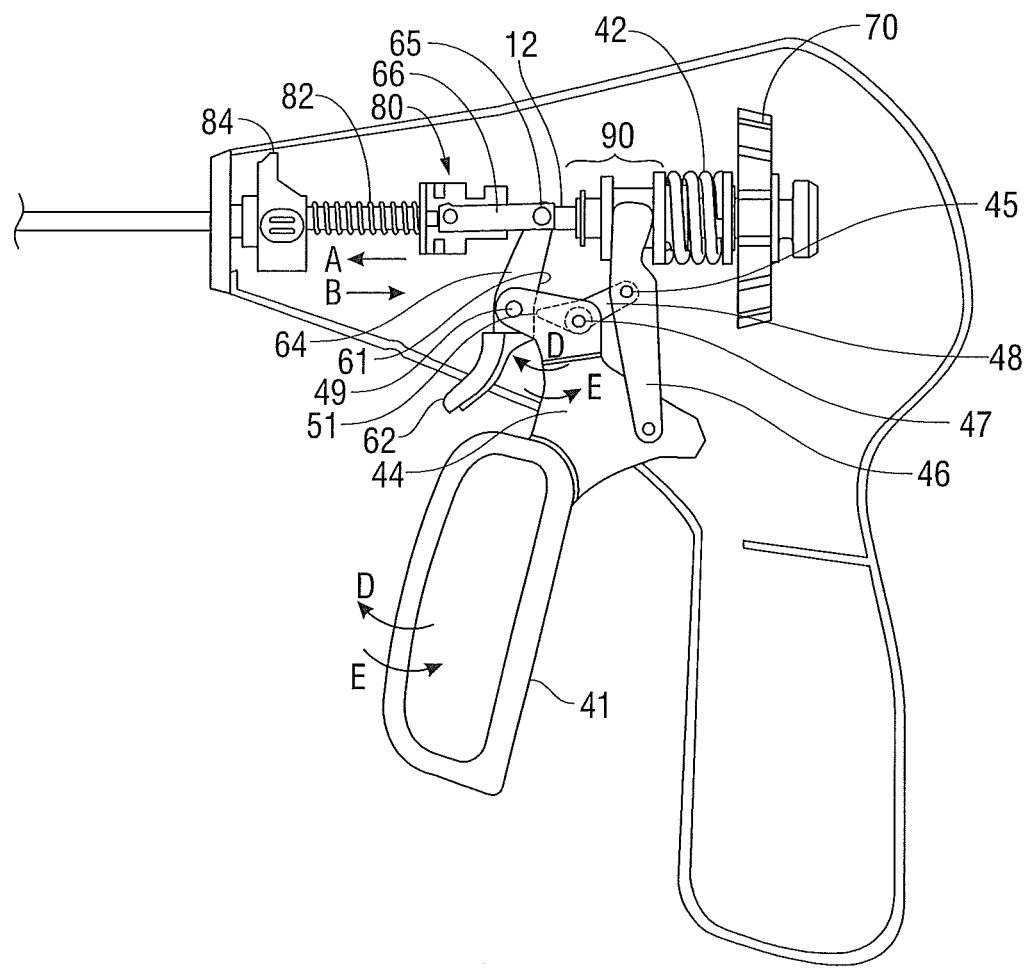
FIG. 2 is a side view of a handle assembly of the forceps of FIG. 1A wherein a portion of a housing has been removed to show internal components of the handle assembly, the handle assembly including a lever and a trigger illustrating a passive lockout feature.

One embodiment of lever assembly 40 is shown including a lever 41 pivotably coupled to housing 20 and extending downwardly therefrom. Lever 41 is ultimately connected to drive assembly 90 (FIG. 2). Lever 41 and drive assembly 90 mechanically cooperate to impart movement of jaw members 110 and 120 between the spaced-apart position (FIG. 1A) and the closed position (FIG. 1B). Other configurations of lever assembly 40 are envisioned for operating drive assembly 90.

Lever 41 is selectively moveable between an initial position (FIG. 1A), and an actuated position relative to integral handle 32 (FIG. 1B) for moving jaw members 110, 120 between the open position shown in FIG. 1A and the closed position shown in FIG. 1B. A biasing device, such as spring 42, is compressed when lever 41 is rotated in direction "E". The spring 42 (FIG. 2) biases lever 41 toward the initial position shown in FIG. 1A in which lever 41 is spaced-apart from handle 32, and jaw members 110, 120 are opened to the open position shown in FIG. 1A.

Figure 3:
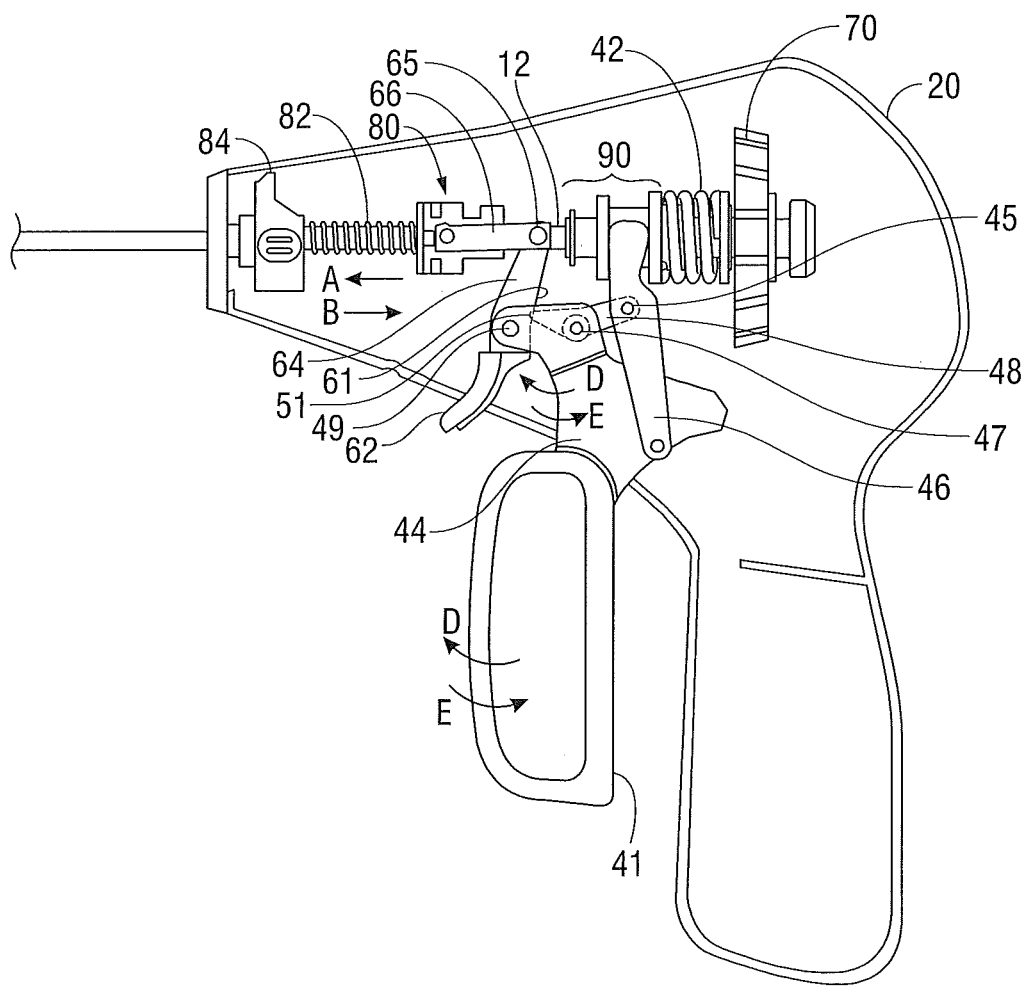
FIG. 3 is a side view of the handle assembly shown in FIG. 2 wherein the lever and trigger illustrating a passive kickback feature.
Figure 4:
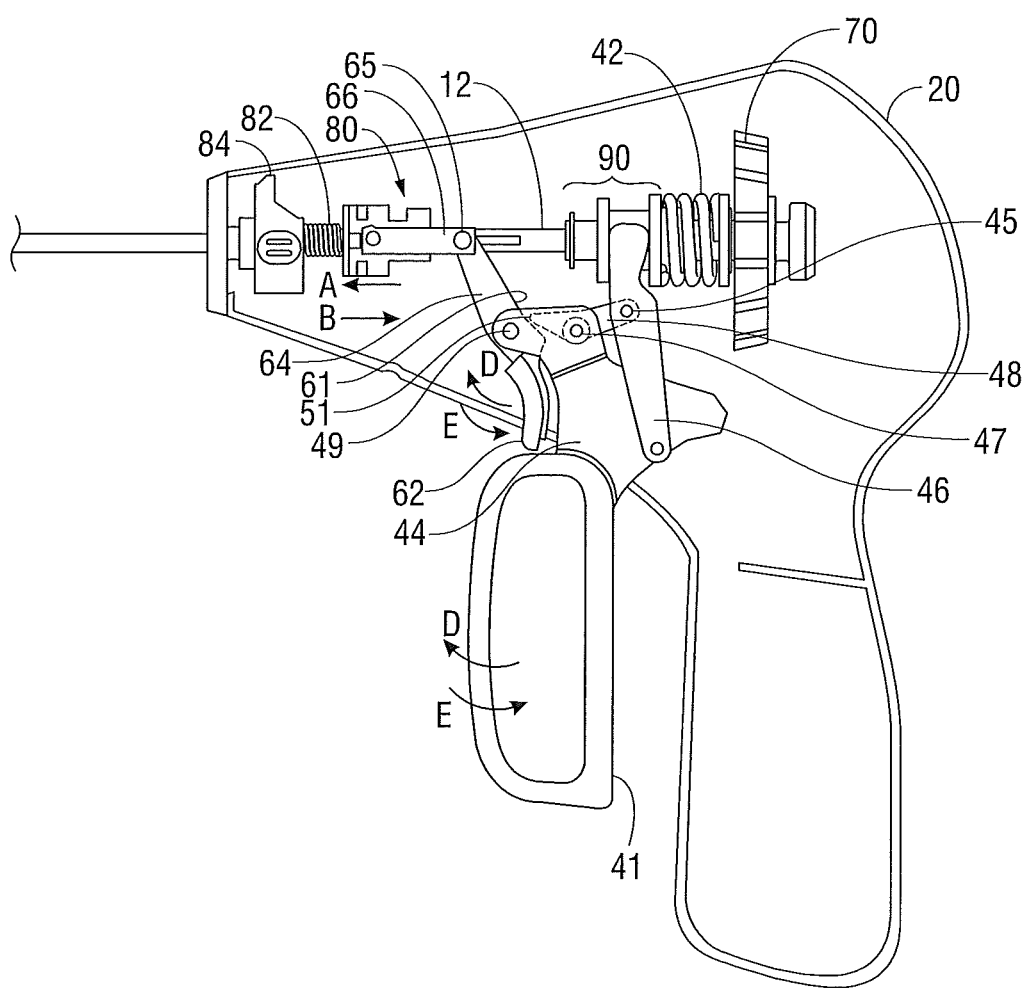
FIG. 4 is a side view of the handle assembly shown in FIG. 2 wherein the lever, trigger and the spindle assembly are each disposed in an actuated position.

Turning now to FIGS. 2-4, trigger 62 is selectively moveable from an initial position (FIGS. 2 and 3), wherein trigger 62 is spaced-apart from "Y"-shaped plate 44 and knife 132 is retracted, to an actuated position (see FIG. 4), wherein trigger 62 is positioned adjacent to plate 44 and knife 132 is deployed. Trigger 62 extends from trigger arm 64. Trigger arm 64 is coupled to plate 44 at joint 49 and to spindle drive arm 66 at joint 65. The spindle drive arm 66 is coupled to spindle assembly 80, and a knife biasing spring 82 is disposed distally of the spindle assembly 80. The knife biasing spring 82 is retained between the spindle assembly 80 and a stop 84 that is stationary relative to the housing 20. Actuation of trigger 62 causes trigger 62 to pivot generally in direction "E" about joint 49 and joint 65, which, in turn, causes spindle drive arm 66 to translate spindle assembly 80 longitudinally in a distal direction "A" along shaft 12, which, in turn, compresses knife biasing spring 82 between spindle assembly 80 and the stop 84. Spindle assembly 80 is operatively coupled to knife 132 (FIG. 1C), such that when spindle assembly 80 is moved distally along shaft 12, knife 132 deploys.

When trigger 62 is actuated, knife biasing spring 82 exerts a spring return force $F_{sr}$ against spindle assembly 80. Upon release of the trigger 62 by the surgeon, spring return force $F_{sr}$ causes trigger 62 to return to its initial position and causes the knife 132 to retract. The surgeon can feel the force exerted on trigger 62 by knife biasing spring 82 and typically controls release of the trigger 62 so that knife 132 is retracted in a controlled manner without undue acceleration. If the trigger 62 were released in an uncontrolled manner, the knife 132 could abruptly return to its retracted position.

FIG. 2 illustrates an exemplary passive safety feature. An exemplary passive safety feature is described in U.S. patent application Ser. No. 13/401,964, filed Feb. 22, 2012, entitled "TRIGGER LOCKOUT AND KICKBACK MECHANISM FOR SURGICAL INSTRUMENTS," which is herein incorporated by reference in its entirety. The passive safety feature includes a lockout feature that locks trigger 62 in its initial position and prevents trigger 62 from being actuated when lever 41 is positioned in its initial position. The lockout feature thus prevents the knife 132 from being deployed when jaw members 110, 120 are spaced apart (FIG. 1A). The lockout feature includes lockout lever 48, which is coupled to plate 44 at joint 47 and to drive lever 46 at joint 45. When the lever 41 is disposed in its initial position, plate 44 and drive lever 46 are arranged such that a distal end 51 of lockout lever 48 abuts a proximal face 61 of trigger arm 64. Lockout lever 48 is positioned such that even when force is applied to trigger 62 in an attempt to actuate trigger 62, such actuation is prevented by interference with lockout lever 48, thus preventing deployment of knife 132.

Other lockout features are envisioned, and the present disclosure is not limited to the above described lockout feature. For example, the lever 41 and trigger 62 may be configured so that when the lever 41 and trigger 62 are in their respective initial positions, the lever 41, or alternatively a handle that operates the lever 41, abuts the proximal face 61 of trigger 62 and prevents actuation of the trigger 62.

The passive safety feature also includes a passive kickback mechanism, shown in FIG. 3, which may be employed when the spring return force $F_{sr}$ is insufficient to return trigger 62 to its initial position and retract the knife 132. This may occur when the knife 132 becomes immobilized. Such immobilization may occur, for example, when knife channel 130 is exposed to tissue and fluids in the surgical sight and becomes sticky, interfering with movement of knife 132 within knife channel 130, when knife 132 becomes misaligned or derailed from knife channel 130, and/or when jaw members 110, 120 clamp down on the knife 132 trapping the knife 132 between the jaw members 110, 120.

In one exemplary scenario in which knife 132 may become trapped between jaw members 110, 112, jaw members 110, 120 are first latched onto a thick tissue bundle without fully closing and knife 132 is deployed. Jaw members 110, 120 may lose their grasp and drop off the tissue bundle, slamming shut due to the force applied by spring 42 as the surgeon continues to pull the lever 41 in direction "E". This may cause jaw members 110, 120 to slam shut on knife 132 while it is still deployed, interfering with return of knife 132 to its initial position.

When the knife 132 is immobilized in a deployed position and the spring return force $F_{sr}$ is insufficient to retract the knife 132, the surgeon can use the passive kickback mechanism to retract the knife 132 by applying a first manual force to lever 41 and/or trigger 62 in direction "D". As lever 41 is moved in direction "D", distal end 51 of lockout lever 48 applies a passive kickback force to the proximal face 61 of trigger arm 64, causing trigger 62 to move in direction "D" and knife 132 to retract. However the knife 132 may be trapped, such that the application of force by the surgeon is unsuccessful in causing application of the passive kickback force, or the passive kickback force is insufficient to free the knife 132 so that it can retract. When this occurs, the lever 41 is immobilized in the actuated position and jaw members 110 and 120, which are closed and may be clamped on tissue, cannot be opened.

This condition is known as device lockup. When device lockup occurs, the jaw members 110, 120 may be stuck in a closed position while knife 132 is trapped in a deployed position. Jaw members 110, 120 may still have a grasp on tissue. When the passive safety mechanism fails to retract the knife 132, the surgeon may apply a second manual force, also referred to as a manual failsafe force, to lever 41 and/or trigger 62 that is even greater than the first manual force. This manual failsafe force is used to activate the mechanical fuse 702 and cause the forceps 10 to failsafe, allowing jaw members 110, 120 to open and release any tissue.

Mechanical fuse 702 includes spindle assembly 80. With reference to FIGS. 5-8, spindle assembly 80 includes a spindle sleeve 504, a spindle cap 502, and a cutter pin 506. Spindle sleeve 504 and spindle cap 502 are both of annular shape. When the spindle sleeve 504 and spindle cap 502 are assembled, they form a first channel 508 defined therebetween which is oriented along the longitudinal direction. Although in the present exemplary embodiment spindle sleeve 504 and spindle cap 502 are shown as separate units, it is envisioned that they could be formed as a single unit. Shaft 12 is received within and extends through first channel 508. Knife rod 134, which is disposed within the longitudinally oriented channel defined within shaft 12, as described above, is thus also received within first channel 508.

Spindle sleeve 504 includes a first portion 512 and a second portion 514. First portion 512 is formed of cylindrically-shaped wall 511, and second portion 514 is formed of cylindrically-shaped wall 513 and annularly-shaped proximal wall 515. An inner surface of wall 511 of first portion 512 defines a portion of channel 508. Second portion 514 has a larger external diameter than an external diameter of first portion 512. An inner surface of cylindrically-shaped wall 513 defines a cavity 519 having a larger diameter than that of channel 508.

Spindle cap 502 includes a cap portion 516 and a cylindrical portion 518 having cylindrical wall 523. An outer diameter of cylindrical portion 518 is dimensioned to fit within cavity 519. Cap portion 516 has an outer diameter that is larger than the diameter of cavity 519 which prevents cap portion 516 from entering cavity 519. When the spindle sleeve 504 and spindle cap 502 are assembled, channel 508 is formed by an inner surface of wall 523 of cylindrical portion 518 of spindle cap 502 and the inner surface of wall 511 of first portion 512 of spindle sleeve 504.

Spindle cap 502 and spindle sleeve 504 have mating features that secure spindle cap 502 to spindle sleeve 504 so that cylindrical portion 518 of spindle cap 502 remains seated within the portion of channel 508 formed by second portion 514 of the spindle sleeve 504. In the embodiment shown in FIGS. 6-10, the mating features include a rib 520 provided on the external surface of wall 523 of cylindrical portion 518 of spindle cap 502 that is configured to match and interface with a corresponding groove 522 provided on the inner surface of wall 513 of second portion 514 of the spindle sleeve 504 that defines cavity 519. Other mating features are envisioned.

Since wall 523 of cylindrical portion 518 of cap 502 is shorter than wall 513 of second portion of spindle sleeve 504, a gap is formed between proximal end 525 of wall 523 and a distal surface 529 of proximal wall 515. The gap forms an annularly-shaped second channel 526 in which cutter pin 506 is disposed. Cutter pin 506 is securely held within second channel 526 under normal operating conditions, thus coupling cutter pin 506 to spindle sleeve 504. As shown, second channel 526 is in communication with first channel 508, and first channel 508 passes through second channel 526.

Second channel 526 is oriented in the transverse direction such that a radius of the annular second channel 526 is normal to the longitudinal axis of the first channel 508. The annular configuration of second channel 526 allows cutter pin 506 to rotate within spindle sleeve 504 when knife rod 134 is rotated (e.g., when shaft 12 and knife rod 134 are rotated by rotating assembly 70, as described above). Thus, with additional reference to FIGS. 2-4, actuation of trigger 62 effects longitudinally-directed movement of spindle assembly 80 which causes longitudinally-directed movement of cutter pin 506 and substantially equivalent longitudinally-directed movement of knife rod 134. In another embodiment, forceps 10 is not provided with a rotating assembly 70 and second channel 526 may be designed to have a different configuration, such as a linear configuration.

Cutter pin 506 is operatively coupled to knife rod 134 and to spindle sleeve 504, thus operatively coupling knife rod 134 to spindle assembly 80. With respect to the coupling of cutter pin 506 to knife rod 134, cutter pin 506 extends transversely through an aperture 521 provided in knife rod 134. Other methods of configuring cutter pin 506 and coupling cutter pin 506 to knife rod 134 are envisioned. For example, cutter pin 506 may be configured as one or more spikes secured to an external surface of shaft 12 or extending from a ring that is mounted on and secured to the external surface of shaft 12.

Knife biasing spring 82 is disposed externally from channel 508 and abuts an external distal face 524 of spindle cap 502. In other embodiments (not shown), the proximal end of knife biasing spring 82 is disposed within channel 508 and abuts an internal, distal side of a proximal wall of spindle cap 502. When knife 132 is deployed, knife biasing spring 82 exerts the spring return force $F_{sr}$ against spindle assembly 80 that urges spindle assembly 80 toward its initial position.

Distal advancement of the spindle assembly 80 and deployment of knife 132 requires the application of a force that exceeds the spring return force $F_{sr}$. Activation of trigger 62 results in application of a force to spindle assembly 80 in direction "A" that exceeds the spring return force $F_{sr}$ and causes distal advancement of the spindle assembly 80 and deployment of knife 132.

In operation, trigger 62 can only be actuated when lever 41 is rotated sufficiently in direction "E" to begin compressing spring 42. The surgeon actuates trigger 62 by moving trigger 62 in a proximal direction "E" which causes trigger 62 to pivot. This causes spindle drive arm 66 (FIGS. 2-4) to move spindle assembly 80 in a distal direction "A" which moves the knife rod 134 in the distal direction "A", thereby causing deployment of knife 132. When the surgeon releases trigger 62, knife biasing spring 82 causes the spindle assembly 80, and thus knife rod 134 and knife 132, to return to their initial positions. However, as described above, device lockup may occur if a trapping force $F_{trap}$ exceeding spring return force $F_{sr}$ and the passive kickback force is exerted on knife 132 and prevents the knife 132 from moving towards its initial position.

In this situation, mechanical fuse 702 allows the forceps 10 to failsafe so that the pair of jaw members 110, 120 may return to its initial, open position and the forceps 10 can be removed from the surgical site. When forceps 10 is locked up, the surgeon may apply a manual force to lever 41 and/or trigger 62 sufficient to overcome trapping force $F_{trap}$ and remove knife 132 from its trapped position. However, if the surgeon does not succeed in releasing the knife 132 from its trapped position by applying the manual force, the surgeon may apply a manual failsafe force, larger than the first manual force, to the lever 41 or trigger 62 to induce the forceps 10 to failsafe as described below.

With reference to FIGS. 2-4 and 7-10, the mechanical fuse 702 and failsafe mode are described. Device lockup may occur during surgical usage when trigger 62 and lever 41 are in the positions shown in FIG. 4 and cutter pin 506 is in the position shown in FIGS. 7 and 8. If knife 132 is trapped and does not return to its initial position via the passive kickback mechanism or the lockout mechanism, and the jaw members 110, 120 are locked in a closed position, the surgeon may apply a large manual failsafe force to trigger 62.

Figure 10:
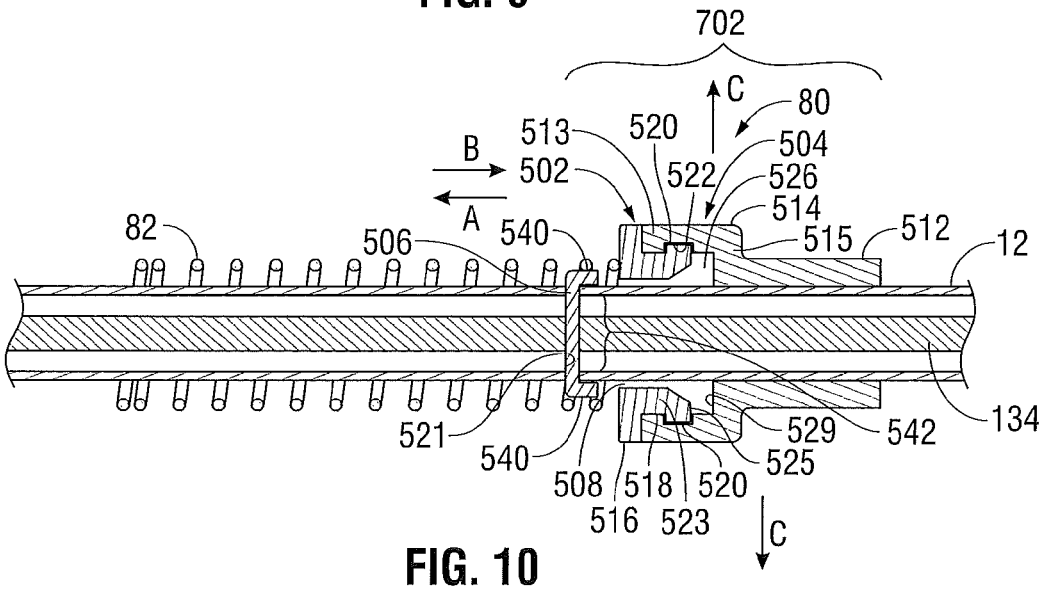
FIG. 10 is a cross-sectional side view of the spindle assembly of FIG. 5 with the cutter pin in an advanced position, having exited the spindle assembly, when the failsafe condition has occurred.

When the surgeon applies a large manual failsafe force to trigger 62 in direction "D", trigger 62 pivots about joint 49 and trigger arm 64 pivots about joint 49, thus pulling spindle drive arm 66 in proximal direction "B". Spindle drive arm 66 pulls spindle assembly 80 in direction "B". This causes proximal end 525 of spindle cap's 502 cylindrical portion's 518 wall 523 to exert a force $F_{spindle}$ against cutter pin 506. When force $F_{spindle}$ exceeds a threshold failsafe force $F_{fs}$, which is the amount of force needed to bend cutter pin 506, cutter pin 506 fails by folding against knife rod 134 as shown in FIG. 10 and extruding out from spindle assembly 80 via channel 508. Cutter pin 506 bends at a middle portion 542 so that when cutter pin 506 is folded, the middle portion 542 is distally located relative to the ends 540 thereof, and the middle portion 542 backs out of the second channel 526 through first channel 508. As cutter pin 506 backs out of first channel 508, spring 82 exerts spring return force $F_{sr}$ on spindle cap 502, pushing spindle assembly 80 in direction "B".

Cutter pin 506 and spindle cap 502 are each configured to allow the failure of cutter pin 506 during device lockup but not during normal use of forceps 10. Cutter pin 506, wall 513 of the cylindrical portion of spindle cap 502, and cylindrical wall 523 of cylindrical portion 518 of spindle sleeve 504 are formed of a deformable material that allows cutter pin 506 to bend, and walls 513 and 523 to flex in a radially outward direction "C" to accommodate the extrusion of cutter pin 506 through the channel 508. Alternatively or additionally, walls 513 and 523 may be formed of a plastic that may deform and/or yield to accommodate the extrusion of cutter pin 506.

Additionally, cylindrical portion 518 of spindle cap 502 has a chamfered portion wherein an inner face 527 of cylindrical wall 523 is sloped to facilitate the extrusion of cutter pin 506. Force $F_{spindle}$ pulls spindle assembly 80 in a proximal direction "B" while cutter pin 506 is immobilized due to the immobilization of knife 132 and knife rod 134. Cutter pins ends 540 are forced against the proximal end 525 of cylindrical wall 523. Since middle portion 542 of cutter pin 506 is coupled to immobilized knife rod 134, the cutter pin 506 is pulled at middle portion 542 which enters channel 508. Due to the chamfered shape of cylindrical wall 523, channel 508 has a diameter that decreases in the distal direction "A" to a diameter that is slightly larger than the outer diameter of shaft 12 and suited to accommodate shaft 12. As middle portion 542 enters channel 508, the inner face 527 of cylindrical wall 523 pushes against ends 540 of cutter pin 506 causing cutter pin 506 to fold. Cylindrical wall 523 and cap portion 516 deflect enough to allow folded cutter pin 506 to exit first channel 508.

It is contemplated that in another embodiment the electrosurgical instrument 10 is configured so that knife biasing spring 82 biases the knife 132 to be disposed in a deployed position, where activation of trigger 62 moves the knife to a retracted position. In this embodiment, the cutter pin 506 may be extracted through a proximal end of spindle assembly 80. The proximal wall defining the second channel 526 would be shaped, such as with a chamfer, to facilitate extrusion of cutter pin 506 from the second channel 526. More specifically, a distal surface 529 of proximal wall 515 would be shaped with a chamfer. The walls of the first portion 512 of the first channel 508 may be configured to flex radially in direction "C" to facilitate extrusion of cutter pin 506 from the first channel 508 and from spindle assembly 80.

Since failure of cutter pin 506 is undesired during normal use of forceps 10, failsafe force $F_{fs}$ must be greater than any forces exerted on cutter pin 506 during normal use, including less than typical circumstances. Such less than typical circumstances may include when there is interference with movement of knife 132 but the knife 132 can still be retracted, albeit with more force than the spring return force $F_{sr}$.

This may occur, for example, when knife channel 134 is exposed to tissue and fluids in the surgical sight and becomes sticky, interfering with movement of knife 132 within knife channel 134. In this circumstance, spring return force $F_{sr}$ exerted by biasing spring 82 may be insufficient to retract knife 132, and the surgeon may need to apply a force greater than spring return force $F_{sr}$ to retract knife 132. The surgeon may do this by applying force to trigger 62 and/or lever 41 for moving trigger 62 in direction "D". However, as long as knife 132 is not trapped and can still be retracted by application of force to trigger 62 by the surgeon, cutter pin 506 should remain engaged in spindle assembly 80 and forceps 10 should not failsafe. Therefore, failsafe force $F_{fs}$ may be selected to be large enough to prevent forceps 10 from failing safe in such a circumstance. In one embodiment, failsafe force $F_{fs}$ is 20 lbf.

In another circumstance, the surgeon may unintentionally release the trigger 62 while the knife 132 is deployed and possibly engaged, but not stuck, in tissue at the surgical site. Knife biasing spring 82 would apply spring return force $F_{sr}$ to spindle assembly 80, moving spindle assembly 80 and knife 132 in direction "B" in an accelerating manner and snapping trigger 62 back to its initial position. Accordingly, $F_{fs}$ may be selected to be sufficiently greater than $F_{sr}$ to avoid failure of the cutter pin 506 upon release of trigger 62 In one embodiment, the spring return force $F_{sr}$ is much less than 20 lbf, even during a knife snapback condition.

Cutter pin 506, wall 513, and wall 523 are configured to set failsafe force $F_{fs}$ at a desired value. Selection of the materials used to form cutter pin 506, wall 513, and wall 523, and their respective shapes may be calculated or determined empirically to achieve the selected failsafe force $F_{fs}$. Selection of the materials forming cutter pin 506, wall 513, and wall 523 includes selecting a material that has a desired degree of resilience and selecting the thickness and shape of the material used. The failsafe force $F_{sr}$ may also be tuned by adjusting heat treatment conditions of cutter pin 506.

In one embodiment, cutter pin 506 is formed of 300 series stainless steel. The cutter pin 506, wall 513, and wall 523 may be formed with features that promote folding of cutter pin 506 and outward deflection of walls 513 and wall 523. For example, cutter pin 506 may be scored or have a decreased thickness at a location of the cutter pin 506 where folding is desired.

In one embodiment, walls 513 and 523 are formed of a deformable plastic material, such as nylon. Walls 513 and 523 may be formed with a decreased thickness at a location of walls 513 and 523 where deflection is desired. Additionally, the slope of inner face 527 may be selected so that extrusion of cutter pin 506 will occur under the desired conditions.

Cutter pin 506 fails in a safe and predictable way, remaining secured to shaft 12 and knife rod 134 by the folded ends 540 as depicted in FIG. 10. Thus, cutter pin 506 cannot fall out of forceps 10, and the risk of foreign material falling into the surgical site is reduced. The failure of cutter pin 506 causes cutter pin 506 to decouple from spindle assembly 80. Once cutter pin 506 is decoupled from the spindle assembly 80, the trigger 62 is decoupled from knife rod 134 and knife 132. Knife rod 134 and knife 132 are safely retained within shaft 12. A stop member (not shown) may be provided on knife 132, knife rod 134, and/or shaft 12 that prevents knife 132 from exiting shaft 12 at the shaft 12's distal end. Spring return force $F_{sr}$ (exerted by biasing spring 82) returns trigger 62 to its initial position, thus allowing the surgeon to operate lever 41 to move jaw members 110, 120 to their open position and release any tissue that was grasped so that forceps 10 can be removed from the surgical site.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A surgical instrument, comprising:
   a housing;
   a shaft having a proximal end positioned within the housing and a distal end positioned remote from the housing, the shaft having a longitudinal axis defined between the proximal and distal ends;
   a pair of jaw members operably coupled to the distal end of the shaft;
   a movable knife rod at least partially disposed within the shaft;
   a knife operably coupled to a distal end of the knife rod;
   an actuator operably coupled to the proximal end of the shaft and moveable relative to the housing between a first position and a second position for moving the jaw members between an open position and a substantially closed position;
   a trigger extending from the housing and configured to actuate the knife; and
   a movable spindle assembly having:
      a body movably disposed on the proximal end of the shaft and operably coupled to the trigger; and
      a cutter pin removably coupled to the body and fixed to the knife rod in an axial position along the knife rod such that actuation of the trigger axially moves the body to effect axial movement of the knife rod,
   wherein upon application of a threshold amount of force on the cutter pin by the body in a proximally-oriented direction, the cutter pin folds such that the cutter pin detaches from the body and the body is movable in a proximal direction relative to the cutter pin and the knife rod.

2. The surgical instrument according to claim 1, wherein the body includes a proximal portion and a distal portion, the cutter pin disposed in a channel defined between the proximal and distal portions of the body such that axial movement of the cutter pin relative to the body is resisted.

3. The surgical instrument according to claim 2, wherein the proximal portion of the body includes a chamfer configured to engage opposing ends of the cutter pin to deform the opposing ends of the cutter pin upon the threshold amount of force being applied by the chamfer on the opposing ends of the cutter pin in a proximally-oriented direction.

4. The surgical instrument according to claim 1, wherein the spindle assembly includes a spindle sleeve and a spindle cap attached to one another.

5. The surgical instrument according to claim 1, further comprising a rotating assembly operably coupled to the housing and configured to rotate the shaft with the knife rod and the cutter pin.

6. The surgical instrument according to claim 1, wherein when the knife is locked in an extended position, retraction of one of the trigger or the actuator using the threshold amount of force causes the body to fold the cutter pin and move away from the cutter pin.

7. The surgical instrument according to claim 1, wherein when the cutter pin is detached from the body, actuation of the trigger does not effect movement of the knife rod.

8. The surgical instrument according to claim 1, further comprising a knife biasing spring disposed within the housing and distally of the body of the spindle assembly to resiliently bias the spindle assembly toward a retracted position, wherein when the cutter pin is detached from the body, the cutter pin is disposed within the knife biasing spring.

* * * * *